United States Patent
Frazier et al.

(10) Patent No.: US 9,073,937 B2
(45) Date of Patent: Jul. 7, 2015

(54) ORGANIC PHOTOVOLTAIC-BATTERY HYBRID DEVICE

(75) Inventors: Rachel M. Frazier, Tuscaloosa, AL (US); Daniel T. Daly, Tuscaloosa, AL (US); Scott K. Spear, Bankston, AL (US); Robin D. Rogers, Tuscaloosa, AL (US); Whitney Hough, Tuscaloosa, AL (US)

(73) Assignee: Board of Trustees of The University of Alabama, Tuscaloosa, AL (US)

( * ) Notice: Subject to any disclaimer, the term of this patent is extended or adjusted under 35 U.S.C. 154(b) by 31 days.

(21) Appl. No.: 13/525,559

(22) Filed: Jun. 18, 2012

(65) Prior Publication Data

US 2012/0318348 A1 Dec. 20, 2012

Related U.S. Application Data

(60) Provisional application No. 61/497,756, filed on Jun. 16, 2011.

(51) Int. Cl.

| | |
|---|---|
| *C07D 487/22* | (2006.01) |
| *C07D 241/46* | (2006.01) |
| *C07D 491/052* | (2006.01) |
| *C07D 209/14* | (2006.01) |
| *H01L 51/00* | (2006.01) |
| *H01L 51/42* | (2006.01) |
| *C07C 309/04* | (2006.01) |
| *C09B 69/02* | (2006.01) |

(52) U.S. Cl.
CPC ............ *C07D 487/22* (2013.01); *C07D 241/46* (2013.01); *C07D 491/052* (2013.01); *C07D 209/14* (2013.01); *H01L 51/005* (2013.01); *H01L 51/0064* (2013.01); *H01L 51/424* (2013.01); *H01L 51/4253* (2013.01); *Y02E 10/549* (2013.01); *C07C 309/04* (2013.01); *C09B 69/02* (2013.01)

(58) Field of Classification Search
CPC .. C07D 487/22; C07D 241/46; H01L 31/0224
USPC ............................ 540/145; 514/185; 136/256
See application file for complete search history.

(56) References Cited

U.S. PATENT DOCUMENTS

| | | | |
|---|---|---|---|
| 6,069,313 | A | 5/2000 | Kay |
| 7,019,209 | B2 | 3/2006 | Spivack et al. |
| 7,196,264 | B2 | 3/2007 | Murai et al. |
| 7,465,834 | B2 | 12/2008 | Sueto et al. |
| 7,466,376 | B2 | 12/2008 | Galvin et al. |
| 7,566,828 | B2 | 7/2009 | Sasaki |
| 7,612,367 | B2 | 11/2009 | Brabec et al. |
| 7,626,509 | B2 | 12/2009 | Dean |
| 7,868,189 | B2 | 1/2011 | Thomas et al. |
| 2005/0196676 | A1 | 9/2005 | Singh et al. |
| 2007/0275546 | A1 | 11/2007 | Maruyama et al. |

FOREIGN PATENT DOCUMENTS

| | | |
|---|---|---|
| EP | 2175512 A1 | 4/2010 |
| WO | 2007/093961 A1 | 8/2007 |
| WO | 2007/111763 A2 | 10/2007 |
| WO | 2009/083901 A1 | 7/2009 |
| WO | 2010/070115 A2 | 6/2010 |

OTHER PUBLICATIONS

Del Sesto et al., Tetraalkylphosphonium-based ionic liquids, J. Organometallic Chem., 690(10):2536-2542 (2005).
Noack et al., The role of the C2 position in interionic interactions of imidazolium based ionic liquids: a vibrational and NMR spectroscopic study, Phys Chem Chem Phys 12(42):14153-14161 (2010).

*Primary Examiner* — Paul V Ward
(74) *Attorney, Agent, or Firm* — Meunier Carlin & Curfman LLC (57) ABSTRACT

Photoactive layers for use in a photovoltaic cell are described. The photoactive layers comprise at least one photoactive ion paired with another ion. This photoactive ion pair can be in the form of an ionic liquid, hydrogen bonded ion pair, cocrystal, or complex to allow for greater flexibility and portability. Also described are photovoltaic cells that contain the described photoactive layers sandwiched between two electrodes.

18 Claims, 7 Drawing Sheets

ORGANIC PHOTOVOLTAIC-BATTERY HYBRID DEVICE

CROSS REFERENCE TO RELATED APPLICATIONS

This application claims the benefit of priority to U.S. Provisional Application 61/497,756, filed Jun. 16, 2011, which is incorporated by reference herein in its entirety.

FIELD

This disclosure generally relates to photovoltaic cells and methods for making and using them.

BACKGROUND

Photovoltaic cells convert light energy (e.g., sunlight) into electricity for a variety of applications. Often used in solar cells, the power production from photovoltaic cells offers a number of advantages such as low operating costs, high reliability, modularity, low construction costs, and of course environmental benefits.

Solar cells convert light into electricity by exploiting the photovoltaic effect that exists at semiconductor junctions. Accordingly, solar cells generally implement semiconductor layers to produce electron current. The semiconductor layers absorb incoming light to produce excited electrons. In addition to the semiconductor layers, solar cells include a front contact electrode to allow the electrons to enter a circuit, and a back contact electrode to allow the ions created by the excitation of the electrons to complete the circuit.

Solar cells based on organic materials have drawn considerable interest in recent times due to the opportunity to decrease cost based on the fact that polymers are cheaper to produce than inorganic semiconductors. Cost per kWhr has been the major market deterrent for widespread use of solar power. Cost can be reduced by using organic-based materials; however, organic-based solar cells are not as efficient as their silicon counterparts. One of the main reasons is due to the types of materials employed in organic photovoltaics (OPVs) and the ability of these materials to effectively generate and transfer electrons and holes (i.e., charge carriers opposite of electrons). The materials that absorb light and transfer electrons (active layers) have been implemented as blends of different materials (bulk heterojunction), stacks of different materials, or adsorbed or chemically attached to inorganic semiconductors (dye-sensitized solar cells). These active layers of OPVs comprise organic-based materials that act as electron donors (donors) or electron acceptors (acceptors). Generally, these donors and acceptors have different dielectric constants, RUB ratios, functional groups, or other property that affects the electrical properties of the materials. Current bulk heterojunction OPVs suffer from phase segregation in the active polymer layers due to mismatch between the donors and acceptors. This creates alternative paths for electrons within the active layer of the solar cells that sacrifice the power output of the cell and diminish the efficiency of the cell. The optimal organic active layer should comprise a homogenous material with donors and acceptors in a nearest neighbor configuration that increases the probability of electron transfer between the donors and acceptors.

Ionic liquids (ILs) play an important role in many electrical devices, including dye-sensitized solar cells (DSSCs), organic light emitting diodes (OLEDs), batteries, and supercapacitors. Currently, ILs are used to transport charge in these devices based on diffusion of ions from one electrode to another through the charge transfer medium known as the electrolyte. This type of use has been applied to solar cells, and in particular DSSCs. These cells use an organic dye to absorb incoming light to produce excited electrons. The DSSC likewise includes two conducting electrodes arranged in a sandwich configuration with a dye-coated inorganic semiconductor film separating the two electrodes. One exemplary technique for fabricating a dye-sensitized solar cell is to coat a conductive glass plate with a semiconductor film such as titanium oxide ($TiO_2$) or zinc oxide (ZnO). The semiconductor layer is usually porous and has a high surface area to allow sufficient amounts of dye for efficient light absorption to be attached as a molecular monolayer on its surface. The semiconductor film is then saturated with a dye and a single layer of dye molecules self-assembles on each of the particles of the semiconductor film, thereby "sensitizing" the film. The remaining intervening space between the electrodes and the pores of the semiconductor film is filled with an electrolyte solution, which may be or may contain a conventional ionic liquid. The electrolyte fills the pores and openings left in the dye-sensitized semiconductor film. The purpose of the electrolyte is to transport the charge generated by the light-excited dye to the electrodes. To complete the solar cell, another electrode is used to provide a cell structure having the dye-sensitized semiconductor and electrolyte sandwiched between the electrode and the conductive glass plate.

It is clear that despite the recent and various advances in photovoltaic materials and devices that contain them, new photoactive materials are still needed. For example, what are needed are materials that absorb within the visible range of the electromagnetic spectrum, can avoid deleterious phase segregation that hampers bulk heterojunction OPVs, are lightweight, flexible, easy to use, and are compatible with fabrication techniques such as spraying, screen-printing, and roll-to-roll processing. The subject matter disclosed herein addresses these and other needs.

SUMMARY

In accordance with the purposes of the disclosed materials, compounds, compositions, articles, devices, and methods, as embodied and broadly described herein, the disclosed subject matter, in one aspect, relates to light-sensitive ion pairs, including ionic liquids, for use in solar cells. Cells and other devices comprising the disclosed light-sensitive ion pairs are also disclosed.

Additional advantages of the disclosed subject matter will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects described below.

DETAILED DESCRIPTION

The devices, compositions, and methods described herein may be understood more readily by reference to the following detailed description of specific aspects of the disclosed subject matter and the Examples included therein and to the Figures.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a layer" includes combinations of two or more such layers, reference to "an electrode" includes combinations of two or more such electrodes, reference to "the cell" includes combinations of two or more such cells, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed as "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Photoactive ion" is an ion that absorbs one or more photons and generates one or more excited electron(s).

The term "aliphatic" is used to refer to a non-aryl hydrocarbon moiety. Aliphatic includes alkyl, alkenyl, alkynyl, cycloalkyl, cycloalkenyl, and cycloalkynyl moieties.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "ion pair" is a positive ion (i.e., cation) and a negative ion (i.e., anion) that are temporarily bonded together by an attractive force (i.e., electrostatic, van-der-Waals, ionic).

The term "ionic liquid" describes a salt with a melting point below 100° C., whose melt is composed of discrete ions.

The term "hydrogen bond" describes an attractive interaction between a hydrogen atom from a molecule or molecular fragment X—H in which X is more electronegative than H, and an atom or a group of atoms in the same or different molecule, in which there is evidence of bond formation. The hydrogen bond donor can be a cation and the hydrogen bond acceptor can be an anion.

The term "co-crystal" describes a crystalline structure made up of two or more atoms, ions, or molecules, that exist in a definite stoichiometric ratio. Generally, a co-crystal is comprised of two or more components that are not covalently bonded and instead are bonded via van-der-Waals interactions, ionic interactions or via hydrogen bonding.

The term "complex" describes a coordination complex, which is a structure comprised of a central atom or molecule that is weakly connected to one or more surrounding atoms or molecules, or describes chelate complex, which is a coordination complex with more than one bond.

The term "eutectic" is a mixture of two or more ionic liquids, ionic liquids and neutral compounds, ionic liquids and charge compounds, ionic liquids and complexes, ionic liquids and ion pairs, or two or more ion pairs that have at least one component in common.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Reference will now be made in detail to specific aspects of the disclosed materials, compounds, compositions, articles, and methods, examples of which are illustrated in the accompanying Examples and Figures.

Photoactive Layer

One of the requirements for a photoactive layer in a solar cell is that it absorbs light within the range of the visible portion of the electromagnetic spectrum. The wide absorption range from 300 nm to 900 nm for common dye salts allows flexibility in tailoring ion pairs, e.g., ILs, to specific wavelengths that are useful for photovoltaic devices. Moreover, the dual nature of ion pairs allows the engineering of new photovoltaic materials by combining donor and acceptor molecules into a single compound without deleterious phase segregation that hampers bulk heterojunction OPVs. Additionally, since ion pairs are lightweight flexible materials, they are easy to use and are compatible with fabrication techniques such as spraying, screen-printing, and roll-to-roll processing. These characteristics make ion pairs extremely amenable to active participation in electrical devices and offer the potential for enhanced device performance and functionality. Moreover, ionic pairs offer the opportunity for eutectic formation, which can be used to create photoactive layers with more than one maximum absorption.

The photoactive layers disclosed herein comprise ion pairs, which include cations and anions in the liquid or solid state or even hydrogen bonded pairs. The disclosed ion pairs contain cations and anions, with at least one of the ions being a photoactive ion. The photoactive ion absorbs light of any wavelength, though preferably in the range of from about 250 nm to about 900 nm, about 300 nm to 800 nm, about 400 nm to about 700 nm, about 350 nm to 850 nm, about 450 nm to 750 nm, about 550 nm to about 900 nm, or about 250 to about 550 nm.

In another embodiment, the disclosed ion pairs contain cations and anions that act as donors and acceptors with optimal HOMO and LUMO energy level differences and optimal distance between ions necessary for highly efficient electron and hole transport between the ions. The appropriate choice of donor ion and acceptor ion exploits the coulombic interaction between the ions to create the optimal distance for electron transfer between the pair. This leads to enhanced electron transfer between the donor and acceptor.

The optimal distance between donor and acceptor can be chosen based on the distance required for non-radiative exciton transfer. Exciton refers to the electron hole pair generated upon illumination within the donor. Energy transfer can happen over short distances by the exciton hopping from donor to acceptor (Dexter energy transfer). This optimal distance is on the order of 1 nm. The choice of donor acceptor pair in this case would have an intermolecular distance of about 1 nm. For example, the ionic radius of the ions would determine the cation-anion (donor-acceptor) distance. These donor and acceptor pairs can be made by metathesis of the salt forms of commercially available dyes. They can also be made by acid-base reactions of the acid and base forms of commercially available dyes. To create liquid forms, metathesis between the salt form of a commercially available dye and the salt form of a long chain fatty acid or a long chain alkyl amine can be done. To form complexes, the donor acceptor pairs can be synthesized using known chelating techniques. Specific examples include Astrazon Orange G proto-porphyrin IX, Astrazon orange—phenyl C61 butyrate, Astrazon orange perylene tetracarboxylate, Methylene Blue dodecyl sulfonate, methylene blue—phenyl C61 butyrate, methylene blue—perylene tetracarboxylate, methylene blue oleate, methylene blue—protoporphyrin IX, Janus Green B dodecyl sulfonate, Janus Green B oleate, Janus Green—phenyl C61 butyrate, Janus Green perylene tetracarboxylate, Janus Green—protoporphyrin IX, Janus Green B—protoporphyrin IX—Cu(II)-oleate, Janus Green B—protoporphyrin IX—Zn(II)-oleate, Janus Green B—protoporphyrin IX—Co(II)-oleate, Janus Green B—protoporphyrin IX—Ag(I)-oleate, Crystal Violet dodecyl sulfonate, Crystal Violet oleate, Crystal violet—phenyl C61 butyrate, Crystal violet—perylene tetracarboxylate, Crystal Violet—protoporphyrin IX, Crystal Violet—protoporphyrin IX—Cu(II)-oleate, Crystal Violet—protoporphyrin IX—Co (II)-oleate, Crystal Violet—protoporphyrin IX—Zn(II)-oleate, Crystal Violet—protoporphyrin IX—Ag(I)-oleate, Astrazon Orange dodecyl sulfonate, Astrazon Orange oleate, Astrazon Orange—protoporphyrin IX—Cu(II)-oleate, Astrazon Orange—protoporphyrin IX—Co(II)-oleate, Astrazon Orange—protoporphyrin IX—Zn(II)-oleate, Astrazon Orange—protoporphyrin IX—Ag(I)-oleate, Basic Yellow 11—dodecyl sulfonate, Basic Yellow 11—oleate, Basic Yellow 11—protoporphyrin IX, Basic Yellow 11—phenyl C61 butyrate, Basic Yellow 11 perylene tetracarboxylate, Basic Yellow 11 protoporphyrin IX—Cu(II)-oleate, Basic Yellow 11 protoporphyrin IX—Co(II)-oleate, Basic Yellow 11 protoporphyrin IX—Zn(II)-oleate, Basic Yellow 11 protoporphyrin IX—Ag(I)-oleate, Astra propyl blue—dodecyl sulfonate, Astra propyl blue—oleate, Astra propyl blue—protoporphyrin IX, Astra propyl blue—phenyl C61 butyrate, Astra propyl blue—perylene tetracarboxylate, Astra propyl blue—protoporphyrin IX—Cu(II)-oleate, Astra propyl blue—protoporphyrin IX—Co(II)-oleate, Astra propyl blue—protoporphyrin IX—Zn(II)-oleate, Astra propyl blue—protoporphyrin IX—Ag(I)-oleate, Rhodamine B—dodecyl sulfonate, Rhodamine B—oleate, Rhodamine B—protoporphyrin IX, Rhodamine B—phenyl C61 butyrate, Rhodamine B—perylene tetracarboxylate, Rhodamine B—protoporphyrin IX—Cu(II)-oleate, Rhodamine B—protoporphyrin IX—Co(II)-oleate, Rhodamine B—protoporphyrin IX—Zn(II)-oleate, Rhodamine B—protoporphyrin IX—Ag(I)-oleate, protoporphyrin IX—Cu(II)-oleate, protoporphyrin IX—Zn(II)-oleate, protoporphyrin IX—Co(II)-oleate, protoporphyrin IX—Ag(I)-oleate.

It is important to distinguish between the ion pairs used in the disclosed photoactive layers from an ionic liquid electrolyte used in some DSSCs. Specifically, in a conventional DSSC, the ionic liquid is used solely as the electrolyte to mediate charge from the dye-sensitized semiconductor (see U.S. Pat. Nos. 7,019,209, 7,196,264, 7,465,834, and 7,868,189). Hence, the dye of the DSSC is not the ionic liquid. The dye absorbs light and generates an excited electron, which is then transported through the ionic liquid by ion diffusion to the electrode (U.S. Pat. No. 7,868,189). The ionic liquid in these devices has a passive role of charge transport and does not absorb light and/or generate the excited electron. Thus none of the ions of such ionic liquids are considered photoactive and the ionic liquid is not considered to be the photoactive layer in a DSSC.

In contrast, the disclosed ion pairs, which can be ionic liquids, in the disclosed photoactive layer act as both the excited electron generator and transporter. At least one of the ions (either the cation or anion or both) is photoactive. The use of the disclosed ionic pairs can provide a system of closely associated electron donors and acceptors to thereby transfer electrons, and not necessarily through ion transport. While not wishing to be bound by theory, possible mechanisms for electron transport include Forster resonance energy transfer or tunneling or hopping between the donor and acceptor.

Ion Pairs with a Photoactive Cation

Examples of photoactive cations that can form part of the disclosed ion pairs include, but are not limited to, Janus Green B, Astrazon Orange G, Crystal Violet, Methyl Violet, Ethyl Violet, Victoria Pure Blue BOH, Bismarck Brown, Malachite Green, Methyl Hreen, Azure C, Sevron Yellow L200, Sevron Brilliant Red 4G, Sevron Brilliant Red B, Sevron Blue 2G, Sevron Black B1, Basic Black PSr, Basic Black RX, Tetrazolium Violet, Rhodamine B, Indoine Blue, and Auramine 0. Additional cations that can be suitable are Color Index (C.I.) Basic Yellow-1, -11, -13, -19, -25, -33, -36, and -51; C.I. Basic Red-1, -2, -9, -12, -13, -14, -28, -38, -39, and -92; and C.I. Basic Blue-1, -3, -5, -9, -19, -24, -25, -26, -28, -41, and C.I. Basic Violet-7 and -10. Protonated porphyrins are also examples of suitable photoactive cations and include, but are not limited to, Zinc 5,10,15,20-tetra(4-pyridyl)-21H,23H-porphine tetrakis(methochloride), Zinc 5,10,15,20-tetra(4-pyridyl)-21H,23H-porphine, Platinum octaethylporphyrin, and Manganese(III) 5,10,15,20-tetra(4-pyridyl)-21H,23H-porphine chloride tetrakis(methochloride). Protonated phthalocyanines are also examples of suitable photoactive cations and include, but are not limited to, Copper(II) 4,4',4'',4'''-tetraaza-29H,31H-phthalocyanine, Gallium(III)-phthalocyanine chloride, Indium(III) phthalocyanine chloride, Iron(II) phthalocyanine bis(pyridine) complex, Iron(III) phthalocyanine chloride, Manganese(III) phthalocyanine chloride, Silicon 2,3-naphthalocyanine dichloride, Silicon phthalocyanine dichloride, and Titanium(IV) phthalocyanine dichloride.

These photoactive cations can be combined with various anions to form an ion pair, which can be in the form of an ionic liquid. Thus, a suitable anion can be one that forms an ionic liquid with the selected photoactive cation. The anion can also be selected to influence the melting point of the ionic liquid (e.g., below 100° C.). Typically, anions with long alkyl chains will lower the melting point of the ionic liquid (Del Sesto et al., *J Organometallic Chem* 690:2536-2542, 2005; Noack et al., *Phys Chem Chem Phys* 12:14153-14161, 2010.)

Alternatively, the melting point can be influenced by the selection of side groups on the cation (Id.). Further, an anion can be selected to facilitate electron transfer (e.g., an anion containing pi bonds). Suitable anions include aliphatic sulfates, aliphatic carboxylates, or aliphatic phosphonates. Sulfonate, phosphonate, or carboxylate anions that contain 1-16 carbon atoms (e.g., formyl, acetyl, propyl, butyl, hexyl, nonyl, decyl, dodecyl, tetradecyl, hexadecyl, maleyl, fumaryl, oxalyl, lactyl, and pyruvyl) can be used. Other suitable anions include, but are not limited to, perfluoroalkyltrifluoroborate, hexafluorophosphate, bis(perfluoroethylsulfonyl)imide, pentafluorophenyl imide, bis((trifluoromethyl)sulfonyl)amide, bis(perfluoroalkylsulfonyl)imide, tris(perfluoralkyl)trifluorophosphates, bis(trifluoromethylsulfonyl)imide, alkyl sulphonates, trihalids and mixed trihalides, alkyl phosphates, alkyl phosphonates, alkyl thiophosphonates, allyl sulphonates, allylphosphonates, allylphosphonates, and the like. Sorbic acid, retinoic acid, dodecyl benzene sulfonic acid, oleic acid, linoleic acid and other fatty acids, especially those with conjugated bonds, can be used as suitable anions.

In a further embodiment, the photoactive cations can be paired with photoactive anions. The photoactive anions and photoactive cations should be chosen considering the differences in highest occupied molecular orbital (HOMO) and lowest unoccupied molecular orbital (LUMO) and the distance between the pair. They should be chosen as effective donors and acceptors where the donor will transfer an electron to the acceptor without losses due to fluorescence, scattering, or inefficient hopping. They should be chosen so as to exploit coulombic interaction to optimize distance between donor and acceptor. These ion pairs offer advantages over organic photovoltaics based on polymers, including improvement in phase segregation, which is envisioned to lead to more efficient electron and hole transport.

Ion Pairs with a Photoactive Anion

Alternatively, the disclosed ion pairs can comprise a photoactive anion. Examples of photoactive anions include, but are not limited to, Bernacid Red 2BMN, Pontamine Brilliant Bond Blue A, Pontamine, Food Black 2, Carodirect Turquoise FBL Supra Cone. (Direct Blue 199, Carolina Color and Chemical), Special Fast Turquoise 8GL Liquid (Direct Blue 86, Mobay Chemical), Intrabond Liquid Turquoise GLL (Direct Blue 86, Crompton and Knowles), Cibracron Brilliant Red 38-A (Reactive Red 4, Aldrich Chemical), Drimarene Brilliant Red X-2B (Reactive Red 56, Pylam, Inc.), Levafix Brilliant Red E-4B (Mobay Chemical), Levafix Brilliant Red E-6BA (Mobay Chemical), Pylam Certified D&C Red #28 (Acid Red 92, Pylam), Direct Brill Pink B Ground Crude (Crompton & Knowles), Cartasol Yellow GTF Presscake (Sandoz, Inc.), Tartrazine Extra Cone. (FD&C Yellow #5, Acid Yellow 23, Sandoz, Inc.), Carodirect Yellow RL (Direct Yellow 86, Carolina Color and Chemical), Cartasol Yellow GTF Liquid Special 110 (Sandoz, Inc.), D&C Yellow #10 (Acid Yellow 3, Tricon), Yellow Shade 16948 (Tricon), Basacid Black X34 (BASF), Carta Black 2GT (Sandoz, Inc.), Neozapon Red 492 (BASF), Orasol Red G (Ciba-Geigy), Direct Brilliant Pink B (Crompton-Knolls), Aizen Spilon Red C-BH (Hodagaya Chemical Company), Kayanol Red 3BL (Nippon Kayaku Company), Levanol Brilliant Red 3BW (Mobay Chemical Company), Levaderm Lemon Yellow (Mobay Chemical Company), Aizen Spilon Yellow C-GNH (Hodagaya Chemical Company), Spirit Fast Yellow 3G, Sirius Supra Yellow GD 167, Cartasol Brilliant Yellow 4GF (Sandoz), Pergasol Yellow CGP (Ciba-Geigy), Orasol Black RL (Ciba-Geigy), Orasol Black RLI (Ciba-Geigy), Orasol Black RLP (Ciba-Geigy), Savinyl Black RLS (Sandoz), Dermacarbon 2GT (Sandoz), Pyrazol Black BG (ICI Americas), Morfast Black Cone A (Morton-Thiokol), Diazol Black RN Quad (ICI Americas), Orasol Blue GN (Ciba-Geigy), Savinyl Blue GLS (Sandoz, Inc.), Luxol Blue MBSN (Morton-Thiokol), Sevron Blue 5GMF (ICI Americas), and Basacid Blue 750 (BASF); Levafix Brilliant Yellow E-GA, Levafix Yellow E2RA, Levafix Black EB, Levafix Black E-2G, Levafix Black P-36A, Levafix Black PN-L, Levafix Brilliant Red E6BA, and Levafix Brilliant Blue EFFA, all available from Bayer; Procion Turquoise PA, Procion Turquoise HA, Procion Turquoise Ho5G, Procion Turquoise H-7G, Procion Red MX-5B, Procion Red H$_8$B (Reactive Red 31), Procion Red MX 8B GNS, Procion Red G, Procion Yellow MX-8G, Procion Black H-EXL, Procion Black P-N, Procion Blue MX-R, Procion Blue MX-4GD, Procion Blue MX-G, and Procion Blue MX-2GN, all available from ICI Americas; Cibacron Red F-B, Cibacron Black BG, Lanasol Black B, Lanasol Red 5B, Lanasol Red B, and Lanasol Yellow 46, bathophenanthroline disulfonic acid disodium salt, and 9,10-Dihydro-9,10-dioxo-2-anthracenecarboxylic acid. Porphyrins are also examples of suitable photoactive anions and include, but are not limited to, 2,3,7,8,12,13,17,18-Octaethyl-21H,23H-porphine iron(III) acetate, 5,10,15,20-Tetrakis(4-hydroxyphenyl)-21H,23H-porphine, 5,10,15,20-Tetrakis(4-sulfonatophenyl)-21H,23H-porphine manganese(III) chloride, Protoporphyrin IX disodium salt, and Protoporphyrin IX zinc (II). Phthalocyanines are also examples of suitable photoactive anions including but not limited to Nickel(II) phthalocyanine-tetrasulfonic acid tetrasodium salt, Iron(III) phthalocyanine-4,4',4",4'''-tetrasulfonic acid, compounds with oxygen monosodium salt hydrate, Copper(II) phthalocyanine-tetrasulfonic acid tetrasodium salt, Copper phthalocyanine-3,4',4",4'''-tetrasulfonic acid tetrasodium salt, and perylene tetracarboxylic acid. Other photoactive anions include C60-carboxylic acid and derivatives of C60.

These photoactive anions can be combined with various cations to form an ionic liquid. A suitable cation can be one that forms an ionic liquid with the selected photoactive anion. The cation can also be selected to influence the melting point of the ionic liquid (e.g., below 100° C.). Typically, cations can be selected to facilitate electron transfer (e.g., a cation containing pi bonds). Examples of cations designed for this purpose include protonated alkyl amines, protonated allyl amines. As noted above, a preferred embodiment has photoactive anions paired with photoactive cations.

Photoactive cations paired with photoactive anions disclosed herein have HOMO/LUMO values that are appropriately matched to the electrodes, i.e., the HOMO/LUMO values of the ions are within 1 eV of the HOMO/LUMO of the electrodes. The HOMO of the cation is separated in energy from the HOMO/work function of the electrode so that ionization of the exciton can occur. This energy difference is in the range of from about 0.1 eV to about 1 eV, e.g., from about 0.1 to about 0.6 eV. The LUMO of the anion is separated in energy from the LUMO/work function of the electrode so that ionization/dissociation of the exciton can occur. This energy difference is in the range of from about 0.1 eV to about 1 eV, e.g., from about 0.1 to about 0.6 eV.

Specific Examples

Some specific examples of suitable photoactive ion pairs are Astrazon Orange G proto-porphyrin IX, Astrazon orange—phenyl C61 butyrate, Astrazon orange perylene tetracarboxylate, Methylene Blue dodecyl sulfonate, methylene blue—phenyl C61 butyrate, methylene blue—perylene tetracarboxylate, methylene blue oleate, methylene blue—protoporphyrin IX, Janus Green B dodecyl sulfonate, Janus Green B oleate, Janus Green—phenyl C61 butyrate, Janus Green—perylene tetracarboxylate, Janus Green—protoporphyrin IX, Janus Green B—protoporphyrin IX—Cu(II)-oleate, Janus Green B—protoporphyrin IX—Zn(II)-oleate, Janus Green B—protoporphyrin IX—Co(II)-oleate, Janus Green B—protoporphyrin IX—Ag(I)-oleate, Crystal Violet dodecyl sulfonate, Crystal Violet oleate, Crystal violet—phenyl C61 butyrate, Crystal violet—perylene tetracarboxylate, Crystal Violet—protoporphyrin IX, Crystal Violet—protoporphyrin IX—Cu(II)-oleate, Crystal Violet—protoporphyrin IX—Co (II)-oleate, Crystal Violet—protoporphyrin IX—Zn(II)-oleate, Crystal Violet—protoporphyrin IX—Ag(I)-oleate, Astrazon Orange dodecyl sulfonate, Astrazon Orange oleate, Astrazon Orange—protoporphyrin IX—Cu(II)-oleate, Astrazon Orange—protoporphyrin IX—Co(II)-oleate, Astrazon Orange—protoporphyrin IX—Zn(II)-oleate, Astrazon Orange—protoporphyrin IX—Ag(I)-oleate, Basic Yellow 11—dodecyl sulfonate, Basic Yellow 11 oleate, Basic Yellow 11 protoporphyrin IX, Basic Yellow 11 phenyl C61 butyrate, Basic Yellow 11 perylene tetracarboxylate, Basic Yellow 11—protoporphyrin IX—Cu(II)-oleate, Basic Yellow 11—protoporphyrin IX—Co(II)-oleate, Basic Yellow 11 protoporphyrin IX—Zn(II)-oleate, Basic Yellow 11 protoporphyrin IX—Ag(I)-oleate, Astra propyl blue—dodecyl sulfonate, Astra propyl blue—oleate, Astra propyl blue—protoporphyrin IX, Astra propyl blue—phenyl C61 butyrate, Astra propyl blue—perylene tetracarboxylate, Astra propyl blue—protoporphyrin IX—Cu(II)-oleate, Astra propyl blue—protoporphyrin IX—Co(II)-oleate, Astra propyl blue—protoporphyrin IX—Zn(II)-oleate, Astra propyl blue—protoporphyrin IX—Ag(I)-oleate, Rhodamine B—dodecyl sulfonate, Rhodamine B—oleate, Rhodamine B—protoporphyrin IX, Rhodamine B—phenyl C61 butyrate, Rhodamine B—perylene tetracarboxylate, Rhodamine B—protoporphyrin IX—Cu(II)-oleate, Rhodamine B—protoporphyrin IX—Co(II)-oleate, Rhodamine B—protoporphyrin IX—Zn(II)-oleate, Rhodamine B—protoporphyrin IX—Ag(I)-oleate, protoporphyrin IX—Cu(II)-oleate, protoporphyrin IX—Zn(II)-oleate, protoporphyrin IX—Co(II)-oleate, and protoporphyrin IX—Ag(I)-oleate.

Photovoltaic Cell

The disclosed photoactive layers can be incorporated into a solar cell. In the disclosed cell, the photoactive layer is sandwiched between the two electrodes, and thus in electrical contact with the electrodes. The electrodes do not make contact with each other. This configuration creates a potential field from the differences in work function of the two electrodes that is manifested within the ion pair by polarizing the charges. This creates an open circuit potential and short circuit current in the dark that is not seen in conventional solar cells but is similar in nature to a double-layer capacitor.

Figure 1:
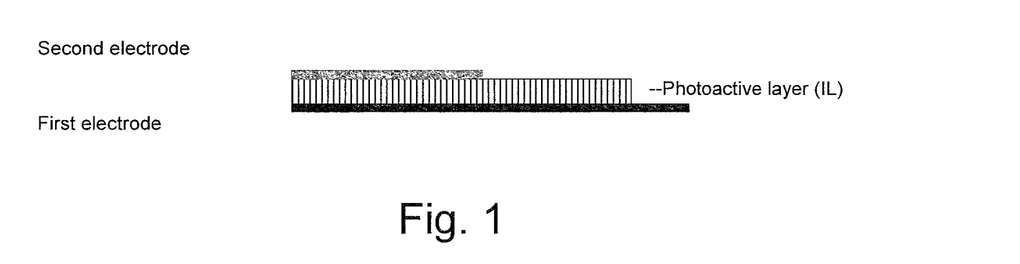
FIG. 1 is a schematic of a portion of a photovoltaic-battery hybrid device disclosed herein.

The disclosed cell comprises three layers: a first electrode, a second electrode, and a photoactive layer between and contacting the first and second electrodes. The photoactive layer, as described herein, has a cation and an anion, one or both of which are photoactive. There general structure of the photovoltaic cell is shown in FIG. 1. The disclosed photovoltaic cells do not contain or are substantially free of a dye-sensitized (i.e., dye coated) semiconductor.

First Electrode

The first electrode, sometimes called a photoanode, can be a conductive material (or material with low resistivity). For example, the first electrode can comprise aluminum, boron, cadmium, chromium, cobalt, copper, gallium, gold, hafnium, iron, indium, manganese, molybdenum, nickel, niobium, palladium, platinum, silver, tantalum, tin, titanium, tungsten, vanadium, zinc, or zirconium, including alloys of and from such materials. In other examples, the first electrode comprises indium tin oxide (ITO), fluorine tin oxide (FTO), indium zinc oxide (IZO), and molybdenum oxide. Glassy carbon, metal oxides, CsCO$_3$, metal borides, metal carbides, graphite, graphene, graphene oxide, nickel mesh, carbon mesh, and the like can also be used. In preferred embodiments, the first electrode can comprise an aluminum alloy, a silver alloy, a copper alloy, lithium alloy, a molybdenum alloy, a chromium/aluminum-neodymium alloy, or a molybdenum/aluminum alloy.

Second Electrode

The second electrode can be a conductive polymeric material. Further, the second electrode can be transparent, semi-transparent, or translucent in order to permit light to enter the cell and excite the photoactive layer. The second electrode can be solid, semi-porous, or porous. In a preferred example, the second electrode is a conductive polymer. The conductive polymer can be chosen from any of the polyacetylene, polypyrrole, polyaniline, poly phenylsulfide, and polythiophenes, including polyethylene dioxythiophene doped with polystyrene sulfonate. Specific examples of conductive polymers include poly(3,4-ethylenedioxythiophene)-poly(styrenesulfonate), poly(3,4-ethylenedioxythiophene), poly(3,4-ethylenedioxythiophene)-block-poly(ethylene glycol), poly(thiophene-3-[2-(2-methoxyethoxy)ethoxy]-2,5-diyl), sulfonated, and polyaniline (emeraldine salt).

Various electrical components can be in electrical communication with at least one of the electrodes of the cell by a means for connecting. A means for connecting can be any material that allows the flow of electricity to occur between one electrode/device and another. A non-limiting example of a means for connecting is a wire comprising a conductive material (e.g., copper, silver, etc.). In some cases, the device can also comprise electrical connectors between two or more components (e.g., a wire and an electrode and/or photoanode). In some cases, a wire, electrical connector, or other means for connecting can be selected such that the resistance of the material is low. In some cases, the resistances can be substantially less than the resistance of the electrodes or photoactive layer.

Further, the cell(s) can be connected to a battery, e.g., a rechargeable battery. The use of batteries can allow for off-grid applications. Others have made solar-powered devices that rely on the combination of a photovoltaic cell with a battery in order that the device can operate at night. Thus, the battery component of these devices stores power provided to it by the photovoltaic cell. In contrast, the cells disclosed herein are a hybrid, having in one device both the solar power generating features of a photovoltaic cell and the power storage features of a battery or capacitor. Thus, power can be supplied at either with or without sunlight, and without the need for an external battery. Thus, in other examples, the disclosed devices do not contain a battery.

In some embodiments, the cell(s) can be connected to an inverter, which converts DC current to AC current. In still other embodiments, the cell(s) can be connected to a power management system, which can be any suitable controller device, such as a computer or microprocessor, and can contain logic circuitry which decides how to route the power streams. The power management system can be able to direct the energy provided from the cell to the end point, for example, another device. It is also possible to feed electrical energy to a power source and/or to consumer devices (e.g., cellular phone, GPS device, radio transmitter/receiver, television/monitor, indoor or outdoor lighting, flash light, signage, and the like).

In some cases, the cell(s) can be connected to a light management system and/or solar concentrator, which are capable of focusing electromagnetic radiation and/or solar energy. Generally, light management systems or solar concentrators can receive electromagnetic radiation and/or solar energy over a surface and direct the received radiation to the cell. Light management systems and solar concentrators are known to those of ordinary skill in the art and can comprise, for example, magnifying lenses, parabolic mirrors, and/or Fresnel lenses for focusing incoming light and/or solar energy. In some cases, the light management system or solar collector can collect and waveguide the light to an area or surface of the cell.

In some cases, the cell alone or with other connected components as disclosed herein can be portable. That is, the device can be of such size that it is small enough that it is movable/portable and can be employed at or near a desired location. In some case, the device can be equipped with straps or other components (e.g., wheels) such that the device can be carried or transported from a first location to a second location. Those of ordinary skill in the art will be able to identify a portable device.

In still other cases, the components of the cell or device are exchangeable, allowing one to replace one or more of the components as needed.

Preferred embodiment is a photoactive layer comprising at least one donor ion paired with at least one acceptor ion. The donor-acceptor ion pair is designed to have the optimal distance between ions to enhance electron transfer and increase efficiency of the photovoltaic cell. In addition, the donor-acceptor ion pair is designed to have the optimal energy differences between the HOMO and LUMO levels between the pair to enhance electron and hole transport between the ions. This photoactive ion pair may be in the form of a liquid to allow for greater flexibility and portability.

Also, disclosed herein are devices that contain one or more of the photovoltaic cells disclosed herein. When more than one of the disclosed photovoltaic cells are present in the device they can be in electrical communication with one another other. For example, a device can contain a housing in which the disclosed cell(s) are located. Preferably, at least a portion of the housing (top and/or side(s)) is substantially transparent to light. During operation, the cell(s) is illuminated through the portion of the housing that is substantially transparent. The housing can also be waterproof.

The disclosed photovoltaic cells can be incorporated into devices that convert solar energy into electricity in order to generate power. Additionally, the disclosed cells can generate power in the absence of sunlight, thereby providing electricity in the dark. The ability to supply current at night is a main advantage of the disclosed cells. In this regard, the disclosed device is unlike other solar cells.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

A donor-acceptor ion pair was made by metathesis of the salt-forms of Astrazon Orange G dye and protoporphyrin IX in acetonitrile. NMR showed a ratio of 1:1 of donor:acceptor. The donor-acceptor pair was found to absorb light with wavelength of 494 nm (Table 1), which falls into the visible spectrum.

Astrazon Orange G

Protoporphyrin IX disodium salt

Example 2

An ionic liquid (IL) was made to demonstrate the formation of a photoactive ionic liquid. A common dye, Janus Green B, was used as the cation of the IL.

This cation was the light-sensitive component of the IL. Janus Green B absorbs in the visible range of the emission spectrum (by UV-Vis spectrophotometry). The anion used was dodecylsulfonate, which is a flexible long-chain alkyl that effectively lowers the melting point temperature. The Janus Green B-dodecylsulfonate IL was made by metathesis of the salt-forms of the dye Janus Green and sodium dodecyl sulfonate:

NMR showed a 1:1.25 molar ratio of Janus Green B to dodecyl sulfonate. To determine purity, the silver nitrate (AgNO$_3$) test was performed and a negative result for chlorine contamination was observed. The transition temperature for the IL was found to be below 100° C. (by differential scanning calorimetry), which falls within the classification of IL.

Example 3

Photoactive ILs similar to that of Example 2 were synthesized by metathesis using the salt forms of Astrazon Orange G as the cation and either dodecylsulfonate or oleate as the anion, Crystal Violet as the cation and either dodecylsulfonate or oleate as the anion, Rhodamine B as the cation and either dodecylsulfonate or oleate as the anion, Basic Yellow as the cation and either dodecylsulfonate or oleate as the anion, or Janus Green B as cation and oleate as the anion (7 ILs total). A photoactive IL was also synthesized using methylene blue and dodecyl sulfonate. See Table 1.

TABLE 1

| Cation | Anion | Form | Form at 50° C. | Tg | $\lambda_{max}$ (UV/Vis) | Purity ($^1$H NMR) Cation:Anion |
|---|---|---|---|---|---|---|
| Astrazon Orange G | Protoporphyrin IX | Solid | Solid | — | 494 nm | 1:0.7 |
| Methylene Blue | Dodecyl Sulfonate | Solid | Solid | 80° C. | | 1:1 |
| Janus Green B | Dodecyl Sulfonate | Solid | | 90° C. | 646 nm | Excess anion (25%) |
| Janus Green B | Oleate | Solid | | — | 645 nm | Excess anion (10-15%) |
| Crystal Violet | Dodecyl Sulfonate | Solid | | >110° C. | 585 nm | 1:1 |
| Crystal Violet | Oleate | Wax | Liquid | 2.45° C. | 585 nm | 1:1 |
| Astrazon Orange | Dodecyl Sulfonate | Solid | | >110° C. | 492 nm | 1:1 |
| Astrazon Orange | Oleate | Liquid | Liquid | 5.15° C. | | 1:3 |

Astrazon Orange G

Rhodamine B

Crystal Violet

Basic Yellow

Figure 2:
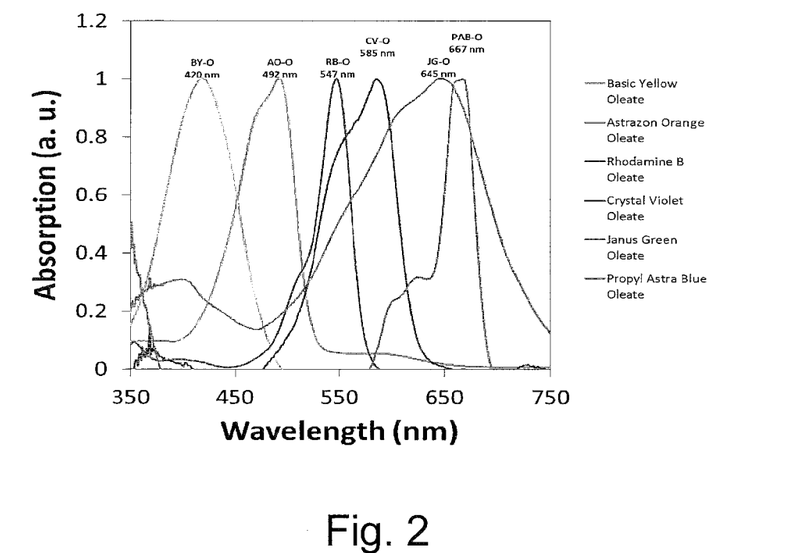
FIG. 2 is a UV/V absorption graph for various photoactive ion pairs.

Each of these compounds absorbs light in the visible portion of the spectrum, as shown in the UV/Vis absorption graph, FIG. 2.

Example 4

Figure 3:
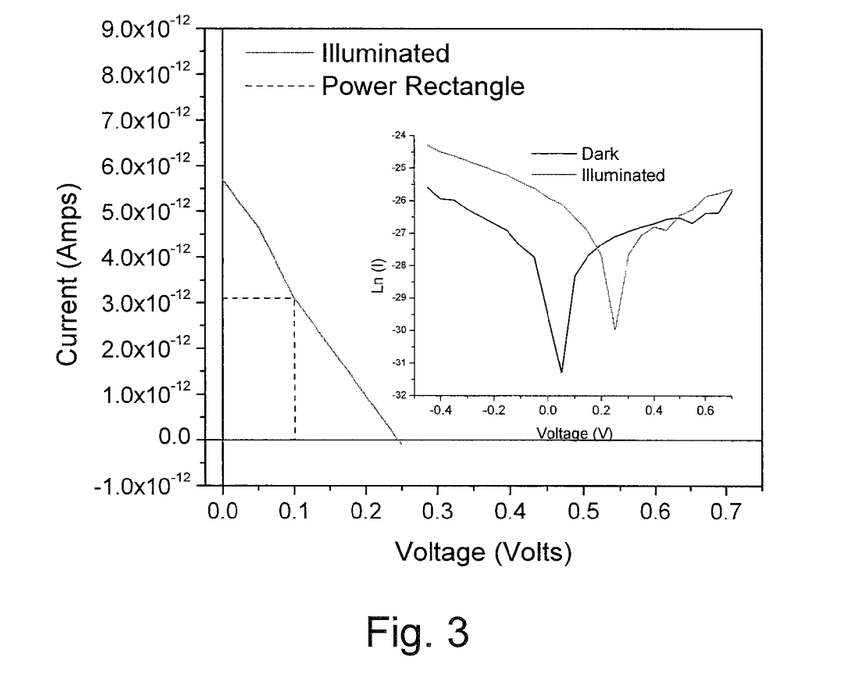
FIG. 3 is a graph showing the IV curve for crystal violet-dodecyl sulfonate in the dark and under illumination of light.
Figure 4:
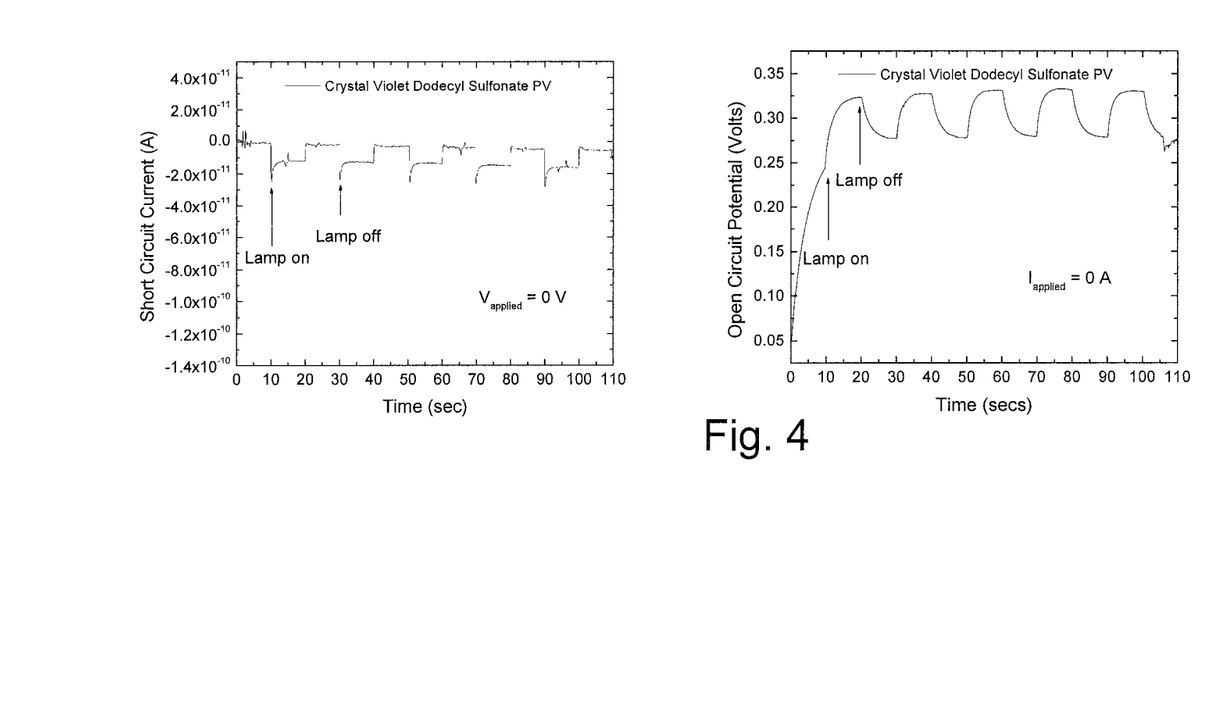
FIG. 4 is a graph showing short circuit current density vs. time and open circuit potential vs. time operation of a photovoltaic-battery hybrid device.

In order to demonstrate the photovoltaic effect, a device was made using the Crystal violet-dodecylsulfonate IL prepared according to Example 3. The photovoltaic device contained the photoactive IL sandwiched between two electrodes, one of which was transparent to light. Indium tin-oxide (ITO) (Sigma-Aldrich, $R_{sh}$ ~120Ω/γ) substrate was used as the transparent electrode. ITO was cleaned by sonicating in isopropyl alcohol, methanol, and acetone. Poly(3,4-ethylenedioxythiophene)-poly(styrenesulfonate) (1.3 wt % solution in water, Sigma-Aldrich; 5 μL/cm$^2$) was coated onto the clean ITO substrate. Crystal violet-dodecyl sulfonate prepared according to Example 3 was dissolved into acetone at a concentration of 70 mg/mL and subsequently coated onto the PEDOT-PSS (5 μL/cm$^2$). A small piece of aluminum foil was used as the top electrode. The electrode area was estimated to be 0.008 cm$^2$. Current-voltage (IV), short-circuit current vs. time, and open circuit potential vs. time were measured using a CH Instruments galvanostat. IV curves in the dark and under illumination of light are shown in FIG. 3, fill factor of about 22%. In order to verify that the short circuit current and open circuit potential in the IV curve corresponds to the photovoltaic effect and not just a capacitance effect, the change in current under no applied potential was measured while alternately exposing the cell to the dark and to illumination. FIG. 4 shows the response of the cell and verifies that the short circuit current changes with illumination. In the same way, the open circuit potential was measured while alternately exposing the cell to the dark and to illumination. FIG. 4 shows that the open circuit potential increases upon exposure to light. The response of the device to illumination verifies the photovoltaic effect.

Example 5

Figure 5:
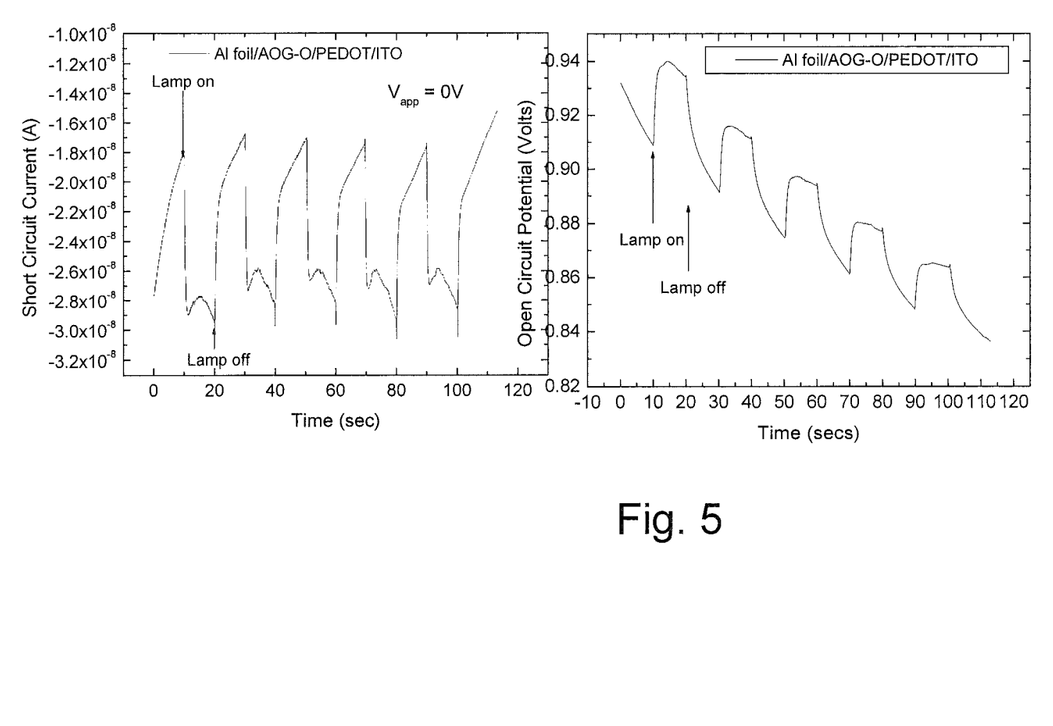
FIG. 5 is a graph showing short circuit current density vs. time and open circuit potential vs. time of a photovoltaic device with a liquid active layer.

Astrazon orange oleate was prepared according to Example 3 and was liquid at room temperature. The $^1$H NMR showed a ratio of 3 oleic acid anions to 1 astrazon orange cation, which may have resulted in the liquid state at room temperature. The liquid Astrazon Orange oleate was used in a photovoltaic device prepared according to Example 4. The response of the device to illumination showed a change in short circuit current and a change in open circuit potential, see FIG. 5.

Photovoltaic cell properties can be optimized by routine optimization known to those skilled in the art. This includes optimizing the materials to allow for more optimal energy differences between the active layer and the electrodes. This includes optimizing the fabrication of the cell to enhance contact between the active layer and the electrodes including, but not limited to, replacing the aluminum foil top electrode with sputtered, electrodeposited, thermal evaporated metal electrode, spin-casting the active layer to optimize thickness of the active layer and increase homogeneity of the active layer, adding cladding layers between the active layer and the electrodes to increase electron transfer and other methods known to those skilled in the art.

Example 6

Figure 6:
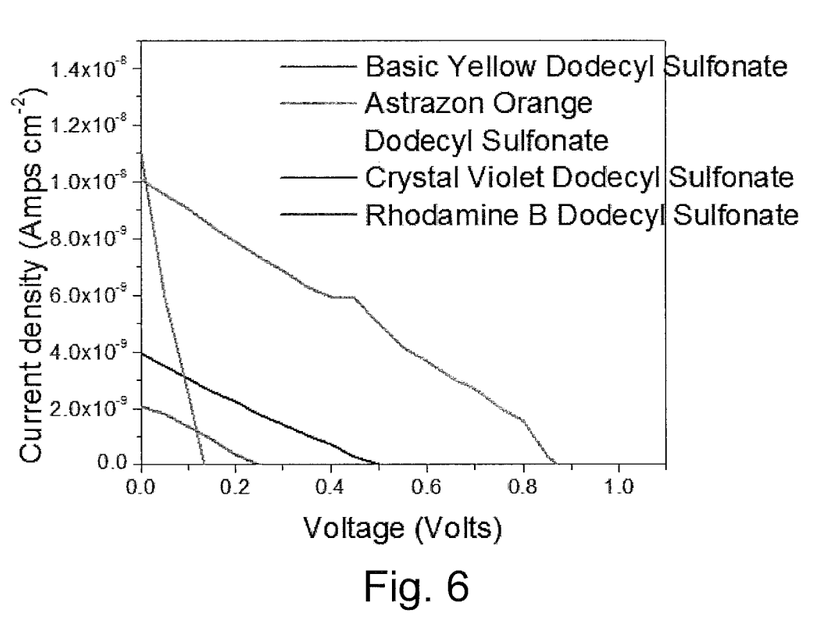
FIG. 6 is a graph showing the IV curves for various cation-docecyl sulfonate ion pairs.
Figure 7:
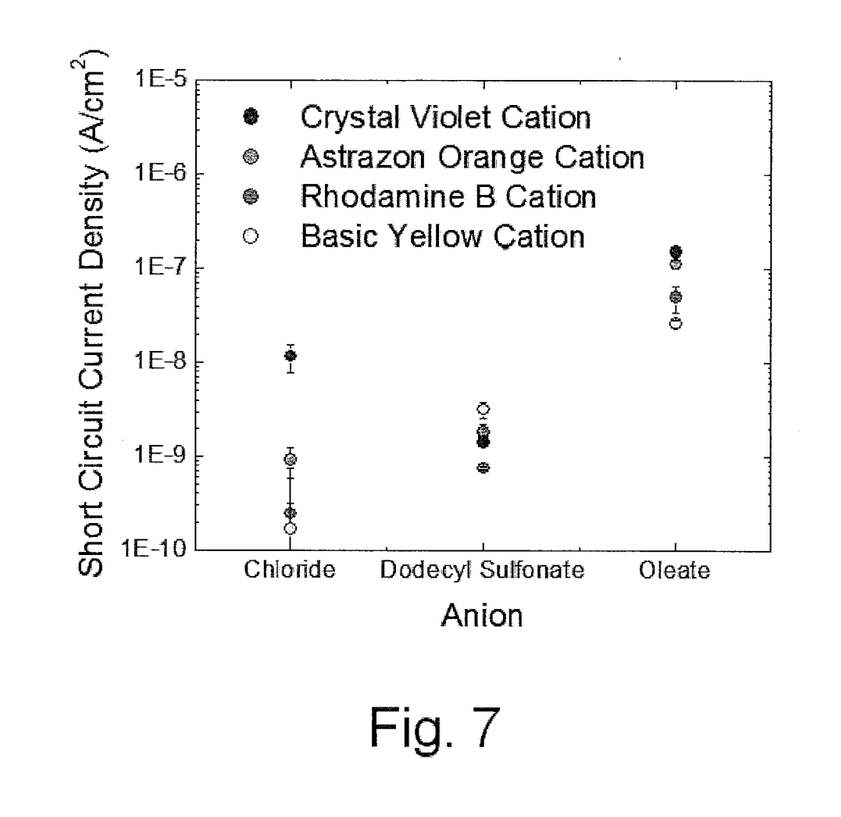
FIG. 7 is a graph showing short circuit current density for various photoactive ion pairs s.
Figure 8:
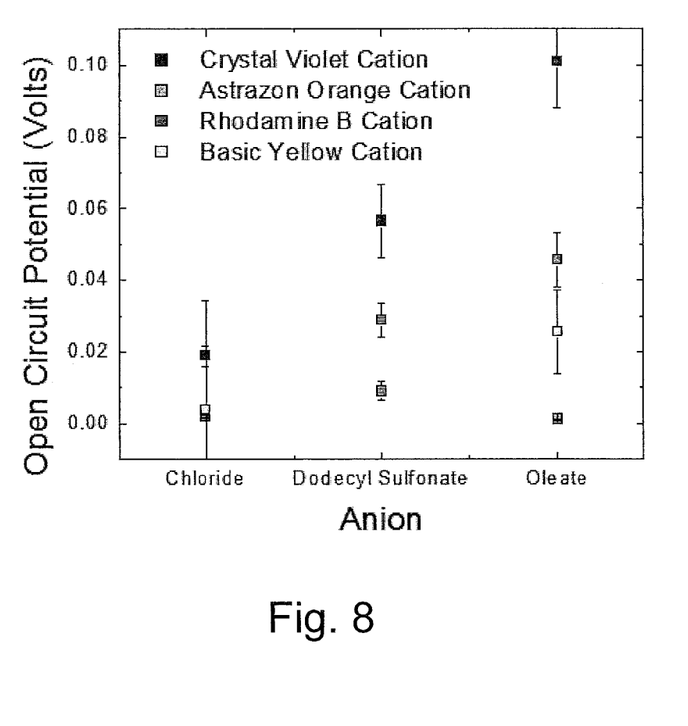
FIG. 8 is a graph showing open circuit current density for various photoactive ion pairs.

In order to demonstrate the improved performance of the ionic liquid versions of the dyes, solar cells were made according to Example 4 from dodecyl sulfonates and oleates prepared according to Example 3. The inverted current voltage curves of the dodecyl sulfonates is shown in FIG. 6. A comparison of the short circuit current vs. anion is shown in FIG. 7. The oleate gives the largest short circuit current, independent of the cation. A comparison of the open circuit voltage is given in FIG. 8.

SPECIFIC EMBODIMENTS

In certain embodiments, disclosed is a photoactive composition that comprises a cation and an anion, wherein the cation, the anion, or both the cation and the anion are photoactive, and wherein the cation and anion form an ion pair, an ionic liquid, are hydrogen bonded, form a complex, or form a cocrystal. In certain examples, the cation is photoactive. In certain examples, the cation absorbs light in a range of from about 400 to about 900 nm and has a HOMO from about 0.1 eV to about 1 eV, e.g., from about 0.1 eV to about 0.6 eV, of the HOMO of the cathode. In certain examples, the anion is photoactive ion. In certain examples, the anion absorbs light in a range of from about 400 to about 900 nm and has a LUMO from about 0.1 eV to about 1 eV, e.g., from about 0.1 eV to about 0.6 eV, of the LUMO of the anode. In certain examples, both the cation and the anion are photoactive. In certain examples, the cation and the anion form an ionic liquid that has a melting point below 100° C. In certain examples, both the cation's and the anion's molecular orbitals are within 1 eV of the molecular orbitals of the corresponding electrodes. In certain examples, wherein the cation and the anion form the ion pair. In certain examples, the composition absorbs light in a range of from about 250 nm to about 900 nm. In certain examples, the cation and the anion form an ionic liquid and the ionic liquid is synthesized by metathesis of salt forms of the cation and the anions or by an acid base reaction.

In certain examples, the cation is Janus Green B, Astrazon Orange G, Crystal Violet, Rhodamine B, Basic Yellow, Protonated porphyrins, or protonated phthalocyanines. Any of these cations can be combined with an anion that is a tetracarboxylic acid functionalized prophyrin, dye-substituted fullerene or graphene, aliphatic sulfate, aliphatic carboxylate, aliphatic phosphonate, oleic acid, linoleic acid, oleate, linoleate, graphene derivative, contains at least one conjugated bond, or contains all conjugated bonds.

In certain examples, the anion is protoporphyrin IX disodium salt, perylene tetracarboxylic acid, Copper(II) phthalocyanine-tetrasulfonic acid, carboxylic derivative of [6,6]-phenyl C61 butyric acid methyl ester, or a fullerene anion. These anions can be combined with a cation that is a protonated aliphatic amine.

Also disclosed is a photovoltaic cell that comprises a first electrode, a second electrode, and a photoactive layer as disclosed herein positioned between and contacting the first and second electrodes. In certain examples, the first electrode comprises aluminum, boron, cadmium, chromium, cobalt, copper, gallium, gold, hafnium, iron, indium, manganese, molybdenum, nickel, niobium, palladium, platinum, silver, tantalum, tin, titanium, tungsten, vanadium, zinc, or zirconium. In other examples, the first electrode comprises an aluminum alloy, a silver alloy, a copper alloy, lithium alloy, a molybdenum alloy, a chromium/aluminum-neodymium alloy, or a molybdenum/aluminum alloy. In certain examples, the second electrode comprises a conductive material that is transparent, semi-transparent, or translucent. In other examples, the second electrode comprises indium tin oxide, fluorine tin oxide, indium zinc oxide, or molybdenum oxide, $CsCO_3$, metal borides, metal carbides, graphene, graphene oxide, nickel mesh, or carbon mesh. In still other examples, the second electrode comprises polyacetylene, polypyrrole, polyaniline, poly phenylsulfide, polythiophenes, or polyethylene dioxythiophene doped with polystyrene sulfonate. In still other examples, the second electrode comprises poly(3,4-ethylenedioxythiophene)-poly(styrenesulfonate), poly(3,4-ethylenedioxythiophene), poly(3,4-ethylenedioxythiophene)-block-poly(ethylene glycol), poly(thiophene-3-[2-(2-methoxyethoxy)ethoxy]-2,5-diyl), sulfonated, or polyaniline (emeraldine salt). Also, disclosed are devices comprising a cell as described herein.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible aspects may be made of the invention without departing from the scope thereof, it is to be understood that all matter herein set forth or shown in the accompanying drawings is to be interpreted as illustrative and not in a limiting sense.

What is claimed is:

1. A photoactive composition comprising a cation and an anion, wherein the cation is Janus Green B, Astrazon Orange G, Crystal Violet, Rhodamine B, or Basic Yellow, wherein the anion is a dye-substituted fullerene or graphene, aliphatic sulfate, aliphatic carboxylate, aliphatic phosphonate, oleic acid, linoleic acid, oleate, linoleate, graphene, or protoporphyrin IX or a salt thereof, and wherein the cation and anion form an ion pair, an ionic liquid, are hydrogen bonded, form a complex, or form a cocrystal.

2. The composition of claim 1, wherein the cation is photoactive.

3. The composition of claim 1, wherein the cation absorbs light in a range of from about 400 to about 900 nm and has a HOMO from about 0.1 eV to about 1 eV of the HOMO of the cathode.

4. The composition of claim 3, wherein the cation has a HOMO from about 0.1 eV to about 0.6 eV of the HOMO of the cathode.

5. The composition of claim 1, wherein the anion is photoactive ion.

6. The composition of claim 1, wherein the anion absorbs light in a range of from about 400 to about 900 nm and has a LUMO from about 0.1 eV to about 1 eV of the LUMO of the anode.

7. The composition of claim 6, wherein the anion has a LUMO from about 0.1 eV to about 0.6 eV of the LUMO of the anode.

8. The composition of claim 1, wherein both the cation and the anion are photoactive.

9. The composition of claim 1, wherein the cation and the anion form an ionic liquid that has a melting point below 100° C.

10. The composition of claim 1, wherein both the cation's and the anion's molecular orbitals are within 1 eV of the molecular orbitals of the corresponding electrodes.

11. The composition of claim 1, wherein the cation and the anion form the ion pair.

12. The composition of claim 1, wherein the composition absorbs light in a range of from about 250 nm to about 900 nm.

13. The composition of claim 1, wherein the cation and the anion form an ionic liquid and the ionic liquid is synthesized by metathesis of salt forms of the cation and the anions or by an acid base reaction.

14. The composition of claim 1, wherein the anion contains at least one conjugated bond.

15. The composition of claim 1, wherein the anion contains all conjugated bonds.

16. The composition of claim 1, wherein the anion is protoporphyrin IX disodium salt, perylene tetracarboxylic acid, Copper(II) phthalocyanine-tetrasulfonic acid, carboxylic derivative of [6,6]-phenyl C61 butyric acid methyl ester, or a fullerene anion.

17. The composition of claim 16, wherein the cation is a protonated aliphatic amine.

18. The composition of claim 1, wherein the cation and anion are selected from the following combinations: Astrazon Orange G protoporphyrin IX, Astrazon orange—phenyl C61 butyrate, Astrazon orange perylene tetracarboxylate, Janus Green B dodecyl sulfonate, Janus Green B oleate, Janus Green B—phenyl C61 butyrate, Janus Green B—perylene tetracarboxylate, Janus Green B—protoporphyrin IX, Janus Green B—protoporphyrin IX—Cu(II)-oleate, Janus Green B—protoporphyrin IX—Zn(II)-oleate, Janus Green B—protoporphyrin IX—Co(II)-oleate, Janus Green B—protoporphyrin IX—Ag(I)-oleate, Crystal Violet dodecyl sulfonate, Crystal Violet oleate, Crystal violet—phenyl C61 butyrate, Crystal violet—perylene tetracarboxylate, Crystal Violet—protoporphyrin IX, Crystal Violet—protoporphyrin IX—Cu(II)-oleate, Crystal Violet—protoporphyrin IX—Co(II)-oleate, Crystal Violet—protoporphyrin IX—Zn(II)—oleate, Crystal Violet—protoporphyrin IX—Ag(I)-oleate, Astrazon Orange dodecyl sulfonate, Astrazon Orange oleate, Astrazon Orange—protoporphyrin IX—Cu(II)-oleate, Astrazon Orange—protoporphyrin IX—Co(II)-oleate, Astrazon Orange—protoporphyrin IX—Zn(II)-oleate, Astrazon Orange—protoporphyrin IX—Ag(I)-oleate, Basic Yellow 11—dodecyl sulfonate, Basic Yellow 11—oleate, Basic Yellow 11—protoporphyrin IX, Basic Yellow 11—phenyl C61 butyrate, Basic Yellow 11—perylene tetracarboxylate, Basic Yellow 11—protoporphyrin IX—Cu(II)-oleate, Basic Yellow 11—protoporphyrin IX—Co(II)-oleate, Basic Yellow 11—protoporphyrin IX—Zn(II)-oleate, Basic Yellow 11—protoporphyrin IX—Ag(I)-oleate, Rhodamine B—dodecyl sulfonate, Rhodamine B—oleate, Rhodamine B—protoporphyrin IX, Rhodamine B—phenyl C61 butyrate, Rhodamine B—perylene tetracarboxylate, Rhodamine B—protoporphyrin IX—Cu(II)—oleate, Rhodamine B—protoporphyrin IX—Co(II)-oleate, Rhodamine B—protoporphyrin IX—Zn(II)-oleate, and Rhodamine B—protoporphyrin IX—Ag(I)-oleate.

* * * * *